United States Patent [19]

Tymiak et al.

[11] Patent Number: 4,754,018

[45] Date of Patent: Jun. 28, 1988

[54] ANTIBIOTIC PREPARED FROM LYSOBACTER SP. SC 14,067 AND ANALOGS THEREOF

[75] Inventors: Adrienne A. Tymiak, Hopewell; Donald R. Kirsch, Princeton; Joseph O'Sullivan, Belle Mead; John E. McCullough, Whitehouse Station, all of N.J.

[73] Assignee: E. R. Squibb & Sons, Inc., Princeton, N.J.

[21] Appl. No.: 23,425

[22] Filed: Mar. 9, 1987

Related U.S. Application Data

[63] Continuation-in-part of Ser. No. 715,802, Mar. 25, 1985, abandoned.

[51] Int. Cl.$^4$ ............................................. C07K 5/12
[52] U.S. Cl. ..................................................... 530/317
[58] Field of Search ......................................... 530/317

[56] References Cited

U.S. PATENT DOCUMENTS 4,393,047  7/1923  Umezawa et al. .................. 424/118
4,588,588  5/1986  Meyers et al. ...................... 424/122

OTHER PUBLICATIONS

Christensen et al., "*Lysobacter* a New Genus of Non-fruiting Gliding Bacteria with a High Base Ratio", *Int. J. Syst. Bacteriol* 28:367–383, 1978.

Ono et al., "Cephabacius, Non Cephom Antibiotics of Bacterial Origin I. Discovery and Taxonomy of the Producing Organisms and Fermentation", *J. Antibiotics*, 37:1528–1535, 1984.

*Primary Examiner*—Delbert R. Phillips
*Attorney, Agent, or Firm*—Lawrence S. Levinson; Donald J. Barrack

[57] ABSTRACT

A novel antibiotic substance EM5587 is prepared by cultivation of a strain of the microorganism Lysobacter sp. SC 14,067, A.T.C.C. No. 53042. Chemical analogs of EM5587 are prepared by chemical synthesis.

8 Claims, 5 Drawing Sheets

ANTIBIOTIC PREPARED FROM LYSOBACTER SP. SC 14,067 AND ANALOGS THEREOF

SUMMARY OF THE INVENTION

This is a continuation-in-part of copending U.S. patent application Ser. No. 715,802, filed Mar. 25, 1985 abandoned.

Cultivation of a strain of the microorganism Lysobacter sp. SC 14,067, which has been deposited in the American Type Culture Collection as A.T.C.C. No. 53042 yields a novel antibiotic substance EM5587. The antibiotic has activity against a range of Gram-positive and Gram-negative bacteria, and has particularly good activity against Gram-positive bacteria.

EM5587 has been analyzed and found to have the chemical structure

It has been given the trivial chemical name "lysobactin".

Gram-positive antibiotic activity is exhibited by chemical compounds having the structure and pharmaceutically acceptable salts thereof. In formula II, and throughout the specification, the symbol "R" refers to hydrogen and acyl. The compounds of formula II have activity against a range of Gram-positive bacteria. The compound of formula II wherein R is hydrogen is also a chemical intermediate useful for preparing compounds of formula II. The compounds of formula II wherein R is acyl also exhibit Gram-negative activity.

As it is used throughout the specification, the term "acyl" includes all organic radicals derived from an organic acid (i.e., a carboxylic acid) by removal of the hydroxyl group. Certain acyl groups are, of course, preferred, but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 17, 1974. The portions of these references describing various acyl groups are incorporated herein by reference. The following list of acyl groups is presented to further exemplify the term "acyl"; it should not be regarded as limiting that term.

Exemplary acyl groups are those derived from natural α-amino acids (including cyclic amino acids). These acyl groups are exemplified by those derived from alanine, arginine, asparagine, aspartic acid, cysteine, cystine, 3,5-dibromotyrosine, 3,5-diiodotyrosine, glutamic acid, glutamine, glycine, histidine, hydroxylysine, hydroxyproline, isoleucine, leucine, lysine, methionine, phenylalanine, proline, serine, threonine, thyroxine, tryptophane, tyrosine and valine.

As it is used throughout the specification, the term "salt" refers to salts formed with inorganic and organic acids. Exemplary inorganic salts are the hydrohalides (e.g., the hydrochloride and hydrobromide), sulfate, nitrate, phosphate, and borate. Exemplary organic salts are the acetate, tartrate, maleate, citrate, succinate, benzoate, pamoate, ascorbate, salicylate, alkane-sulfonates (e.g., methanesulfonate) and arylsulfonates (e.g., benzenesulfonate). The nontoxic, pharmaceutically acceptable salts are preferred, although other salts are also useful, e.g., in isolating or purifying the product. Salts can be prepared by passage of a water-acetonitrile (1:1 v/v) solution of the antiobiotic through a basic ion exchange resin, e.g., AG MP-1 (Bio-Rad, Richmond, Calif.), in the appropriate anionic form.

DETAILED DESCRIPTION OF THE INVENTION

The Microorganism:

The microorganism used for the production of EM5587 is a strain of Lysobacter sp. SC 14,067. A subculture of the microorganism can be obtained from the permanent collection of the American Type Culture Collection, Rockville, Md. Its accession number in this repository is A.T.C.C. No. 53042. In addition to the specific micoorganism described and characterized herein, it should be understood that mutants of the microorganism (e.g., mutants produced through the use of x-rays, ultraviolet radiation, or nitrogen mustards) can also be cultivated to produce EM5587.

Isolation of Lysobacter sp. SC 14,067 from a sample of wet leaf litter (in this instance obtained from a stream in Washington's Crossing State Park, N.J.) in which it is present can be accomplished by plating the soil onto Littman's agar (BBL Microbiology Systems, P.O. Box 243, Cockeysville, Md. 21030) supplemented with a sterile streptomycin solution so the final concentration is 30 μg/ml of medium.

After 6 days incubation at about 25° C., the colonies of Lysobacter sp. SC 14,067 are isolated from the plated sample. The isolated colonies are picked off onto an agar medium composed of:

| Yeast extract | 5.0 g |
|---|---|
| Glucose | 5.0 g |
| MgSO$_4$.7H$_2$O | 0.1 g |
| FeSO$_4$.7H$_2$O | 0.1 g |
| Agar | 17.5 g |
| Tap water | 800 ml |
| Soil extract filtrate* | 200 ml |

*The soil extract filtrate is made by boiling a suspension of soil in water (1:2, w/v) for 1 hour and filtering the cooled extract.

The medium is sterilized in an autoclave at 121° C. for 30 minutes.

Lysobacter sp. SC 14,067 is a Gram-negative rod that exhibits varying morphology depending on the medium. In trypticase-soy agar, the cells are short rods with rounded ends and are fairly uniform in length. On 0.2% tryptone agar, the rods are thin, slightly flexuous and range in length from about 0.4–40 μm. On this medium, they exhibit characteristic gliding motility. No fruiting bodies are formed. Colonies are slimy or mucoid and a dirty yellow in color.

On Hugh-Leifson's O/F glucose test, (J. Bacteriol., 66: 24 (1953)), Lysobacter sp. SC 14,067 grows oxidatively, but no acid production is evident. The weak acid production is masked by ammonia from the peptone in the medium. On Board and Holding's peptone-free medium (Manual of Methods for General Bacteriology, eds. Gerhardt et al., A.S.M., Washington, D.C., 1981, p. 433) with monobasic ammonium phosphate at 0.05% as nitrogen source and 0.5% glucose as the sole carbon source, detectable acid is produced. The organism is cytochrome oxidase, catalase and phosphatase positive.

Lysobacter sp. SC 14,067 is chitinolytic and lyses cells of yeasts, e.g., Saccharomyces. It is strongly proteolytic on gelatin and casein. No cellulolytic or agarolytic activity is evident. Tests for indole, methyl red and the Voges-Proskauer reaction are all negative. The mole % G+C of Lysobacter sp. SC 14,067 DNA is 64.9.

The above characteristics are all consistent with those of members of the genus Lysobacter as described by Christiansen and Cook (1978) Int. J. Bacteriol. 28 (3): 376–393.

The Antibiotic EM5587:

The antibiotic EM5587 can be produced by cultivating Lysobacter sp. SC 14,067, A.T.C.C. No. 53042, at, or near, 25° C. under submerged aerobic conditions in an aqueous nutrient medium containing assimilable carbohydrate and nitrogen sources. The fermentation is carried out until substantial activity is imparted to the medium, usually about 24–28 hours.

After the fermentation is completed, the broth is centrifuged to separate the cells of the producing microorganism from the fermentation supernate. EM5587 is present in both the solid and liquid portions. The solids are extracted with acetone-water (4:1) and the extract is concentrated in vacuo to an oily residue. The residue is triturated with a minimal amount of methanol and the methanol soluble material is chromatographed on a column of MCI gel CHP20P*, eluting with water-acetonitrile-trifluoroacetic acid mixtures. Fractions active against Staphylococcus aureus that are homogeneous by TLC are combined. Crystallization can be achieved by evaporation of acetonitrile-water-trifluoroacetic acid solutions of EM5587 under a stream of nitrogen. The crystalline EM5587 trifluoroacetate salt is collected by vacuum filtration. The broth supernate is adjusted to pH 7.0, and is extracted with n-butanol. The butanol extract is concentrated in vacuo and then triturated and chromatographed in the same manner as described for the cell extract to provide EM5587 as its trifluoroacetate salt.

*MCI gel CHP20P is a macroreticular styrenedivinylbenzene copolymer manufactured by Mitsubishi Chemical Industries, Ltd.

Other salts can be prepared by passage of a water-acetonitrile (1:1, v/v) solution of EM5587 trifluoroacetate salt through a basic ion exchange resin, e.g., AG MP-1 (Bio-Rad, Richmond, Calif.), in the appropriate anionic form.

Chemical Synthesis of Compounds of Formula II

Using EM5587 as a starting material, compounds of formula II wherein R is acyl can be prepared via the compound of formula II wherein R is hydrogen.

The compound of formula II wherein R is hydrogen can be obtained by cleaving the N-terminal leucine residue of EM5587 using classical peptide degradation methodology (e.g., Edman degradation). The N-terminal amino group of EM5587 reacts with phenylisothiocyanate in aqueous base (e.g., pyridine) to form the phenylthiocarbamyl derivative of EM5587. Excess reagent and other apolar products are removed by extraction (e.g., with toluene) and the phenylthiocarbamyl derivative of EM5587 is lyophilized. Treatment of the phenylthiocarbamyl derivative of EM5587 with acid (e.g., trifluoroacetic acid) cleaves the N-terminal amino acyl residue from the peptide as a thiazolinone which is removed by extraction (e.g., diethyl ether), yielding desleucyl EM5587 (i.e., the compound of formula II wherein R is hydrogen).

Well known acylation techniques can be used to convert desleucyl EM5587 to a compound of formula II wherein R is acyl. Exemplary techniques include reaction with a carboxylic acid or corresponding carboxylic acid halide or carboxylic acid anhydride in an organic solvent (e.g., dimethylformamide). The reactions with a carboxylic acid proceed more readily in the presence of a carbodiimide such as dicyclohexylcarbodiimide and a substance capable of forming a reactive intermediate in situ such as N-hydroxybenzotriazole or 4-dimethylaminopyridine. In those instances wherein the acyl group contains reactive functionality (such as amino or carboxyl groups) it may be necessary to first protect these functional groups, then carry out the acylation reaction, and finally deprotect the resulting product. Deprotection can be accomplished using art recognized techniques. If an amino group is protected as a benzyloxycarbonyl derivative, catalytic (e.g., palladium on charcoal) hydrogenation can be used.

The acylated products of formula II can be purified by chromatography on reversed phase resin (e.g., MCI gel CHP20P) eluting with water-acetonitrile-trifluoroacetic acid mixtures. Fractions active against a Gram-positive microorganism, e.g., *Staphylococcus aureus* or *Bacillus subtilis*, that are homogeneous (as shown by thin layer chromatography) can be combined and lyophilized.

Compounds of formula II, and pharmaceutically acceptable salts thereof, can be used as agents to combat bacterial infections (particularly Gram-positive infections) in mammalian species, such as domesticated animals (e.g., dogs, cats, cows, horses and the like) and humans. They can be administered using modes of administration which have been used in the past to deliver penicillins and cephalosporins to the site of the infection. Such methods of administration include intravenous, intramuscular and as a suppository. The dosage of the antibiotic of formula II used will, of course, vary with the particular antibiotic, the size of the host and the severity of the infection. For a human adult, daily doses of about 250 milligrams to about 2 grams are exemplary. Further information about the potency of the compounds of this invention is set forth below under the heading "Biological Activity".

The following examples further describe the preparation and utility of the compounds of this invention.

EXAMPLE 1

EM5587, trifluoroacetate salt

Lysobacter sp. SC 14,067, A.T.C.C. No. 53042, was maintained on the following sterilized agar medium (A):

| Medium A | |
| --- | --- |
| Yeast extract | 5.0 g |
| Glucose | 5.0 g |
| MgSO$_4$.7H$_2$O | 0.1 g |
| FeSO$_4$.7H$_2$O | 0.1 g |
| Soil extract filtrate* | 200 ml |
| Agar | 17.5 g |
| Tap water | 800 ml |

*Soil extract filtrate was prepared by mixing 1 volume of soil with 2 volumes of water at 100° C. for one hour followed by filtration. The medium was sterilized at 121° C. for 15 minutes at 15 lbs steam pressure prior to use.

A loopful of surface growth from an agar slant (Medium A) of Lysobacter sp. SC 14,067, A.T.C.C. No. 53042, was used to inoculate each of two 500 ml Erlenmeyer flasks each containing 100 ml of the following sterilized medium B:

| Medium B | |
| --- | --- |
| Yeast extract | 5.0 g |
| Peptone | 3.0 g |
| Mannitol | 5.0 g |
| Distilled water to | 1.0 liter |

The medium was sterilized at 121° C. for 15 minutes prior to use.

After inoculation, the flasks were incubated at 25° C. on a rotary shaker (300 rpm; 2 inch stroke) for approximately 24 hours. Transfers of 1% (vol./vol.) were made from the grown culture flasks to fifty 500 ml Erlenneyer flasks each containing 100 ml of sterilized medium B as described above. After inoculation, the flasks were once again incubated at 25° C. on a rotary shaker (as previously described) for approximately 24–28 hours. At this time the contents of the flasks were combined and the broth was centrifuged yielding approximately 4.8 liters of supernatant broth and 33 g of cells (wet weight).

The cell mass (33 g) was extracted with three 200 ml portions of acetone water (4:1). The filtered extracts were combined and concentrated to dryness. The residue was triturated with methanol and the soluble portion was concentrated to a yellow glass (705 mg). Chromatography of the methanol soluble material was accomplished on a 2.5×43 cm column of MCI gel CHP20P, with a linear gradient prepared from 1 liter of 0.1% trifluoroacetic acid in water and 1 liter of 0.1% trifluoroacetic acid in acetonitrile. Fractions giving a single Rydon-positive component by TLC (Merck silica gel-60; n-butanol-acetic acid-water 4:1:1; Rf=0.42) were combined and dried to yield an off-white solid (173 mg). The solid was dissolved in acetonitrile-water-trifluoroacetic acid (50:50:0.1) and left to evaporate under a stream of nitrogen to afford 73 mg of crystalline EM5587 as its trifluoroacetate salt.

Elemental analysis was performed on a sample after drying in vacuo at 70° C. for 3 hours. Found: C, 50.01; H, 6.92; N, 13.98; F, 7.4.

Figure 1:
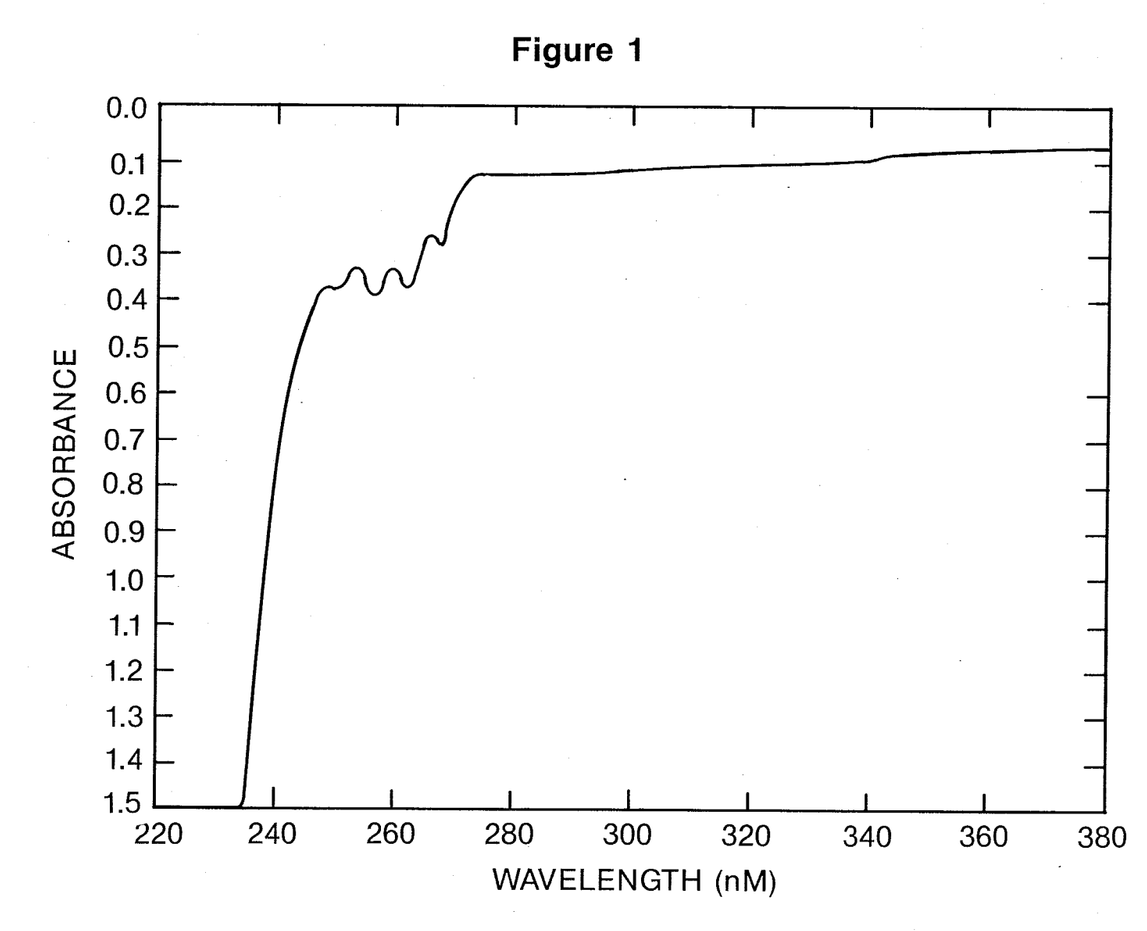
FIG. 1 shows the ultraviolet spectrum of the trifluoroacetate salt of EM5587 in methanol.

The ultraviolet spectrum of the trifluoroacetate salt of EM5587 is presented in FIG. 1 and shows: λmax (E$_1$ cm$^1$%) 250 (sh, 1.4), 257 (1.5), 262 (1.4) and 268 nm (0.9) in addition to end absorption.

Figure 2:
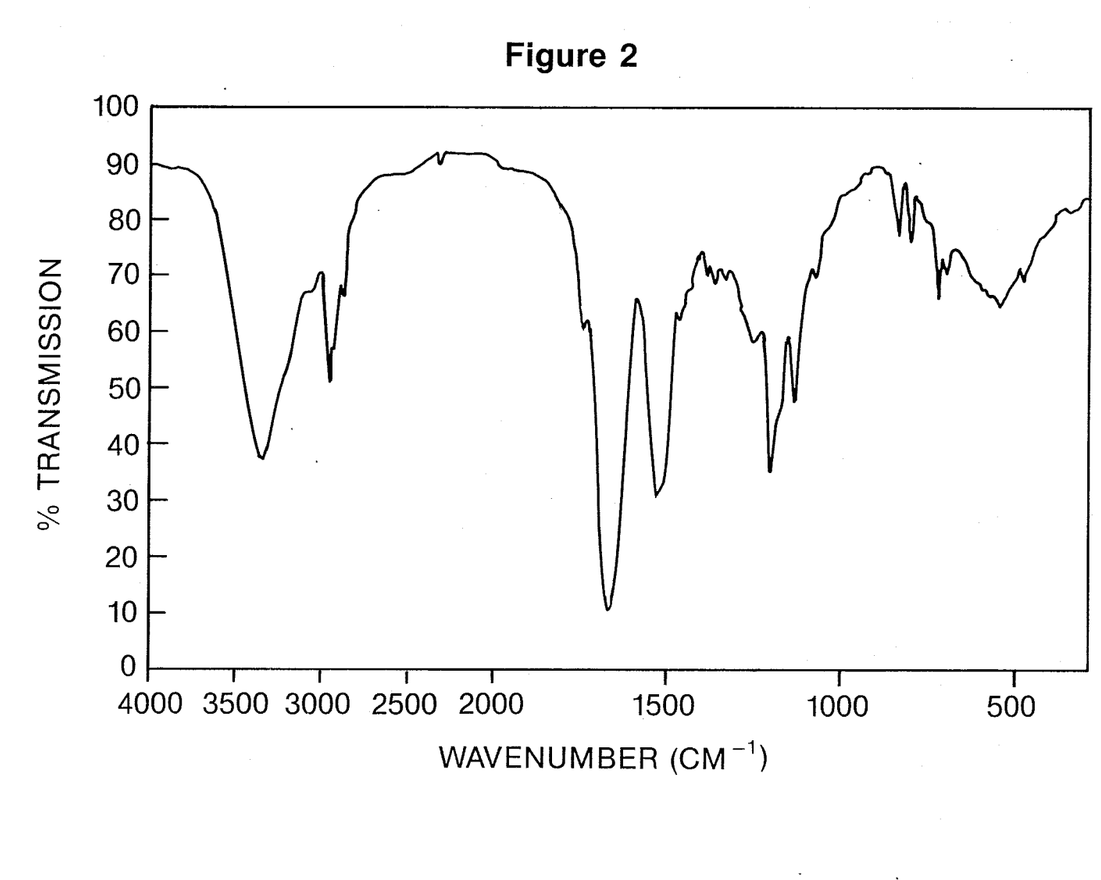
FIG. 2 shows the infrared spectrum of the trifluoroacetate salt of EM5587 in potassium bromide.

The infrared spectrum of the trifluoroacetate salt of EM5587 in potassium bromide is shown in FIG. 2. The following peaks are evident: 3345 (br), 2965, 2937, 2878, 1745 (w), 1666 (s), 1530 (s), 1203, 1138, 838, 800, 722, and 702 cm$^{-1}$.

Figure 3:
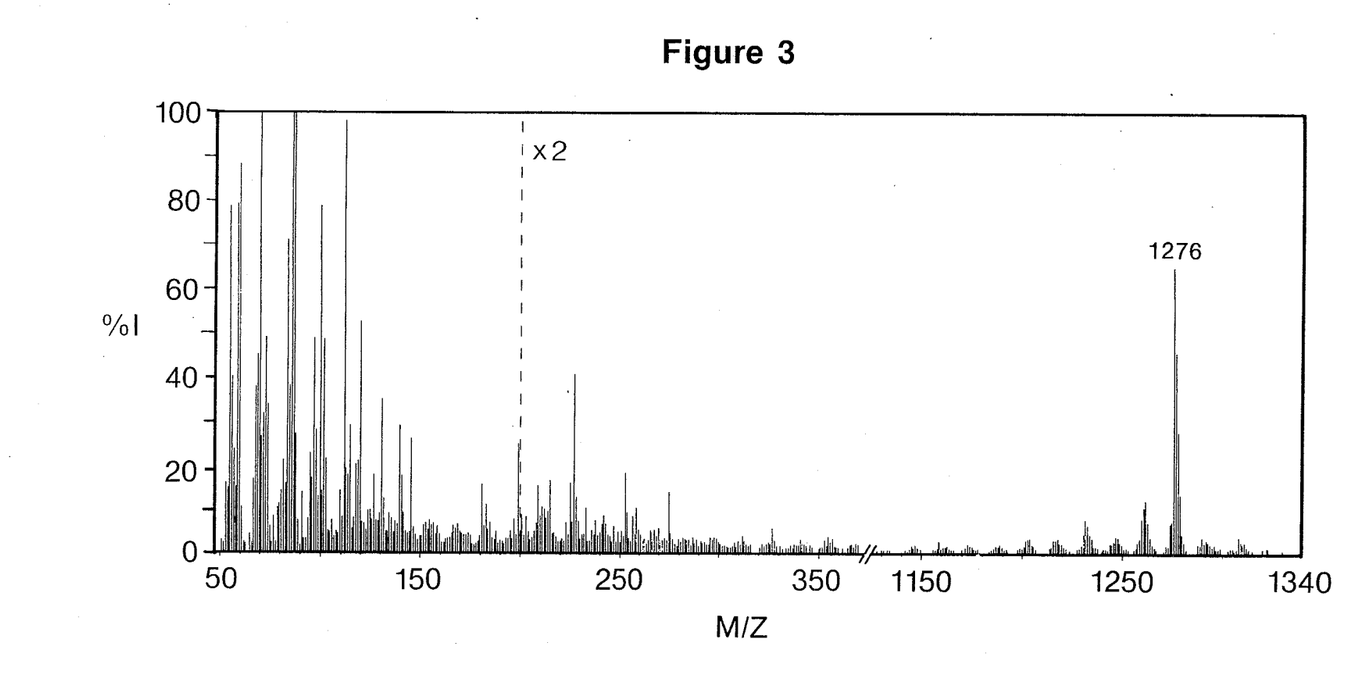
FIG. 3 shows the fast atom bombardment mass spectrum of the trifluoroacetate salt of EM5587 in the positive mode.

The FAB mass spectrum of the trifluoroacetate salt of EM5587 in dithiothreitol-dithioerythritol is shown in FIG. 3.

Figure 4:
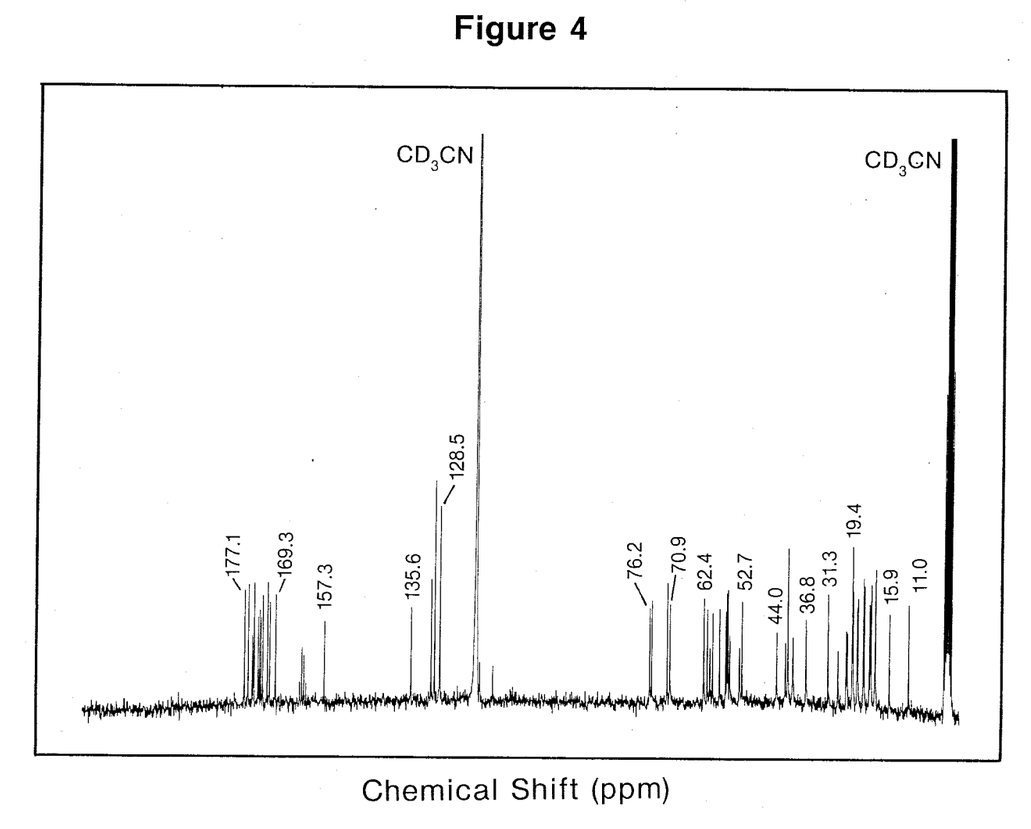
FIG. 4 shows the 67.5 MHz $^{13}$C NMR spectrum of the trifluoroacetate salt of EM5587 in deuterated acetonitrile-deuterated water-trifluoroacetic acid (50:50:0.1).

The 67.5 MHz $^{13}$C NMR spectrum of the trifluoroacetate salt of EM5587 in deuterated acetonitrile-deuterated water-trifluoroacetic acid (50:50:0.1) is shown in FIG. 4.

Figure 5:
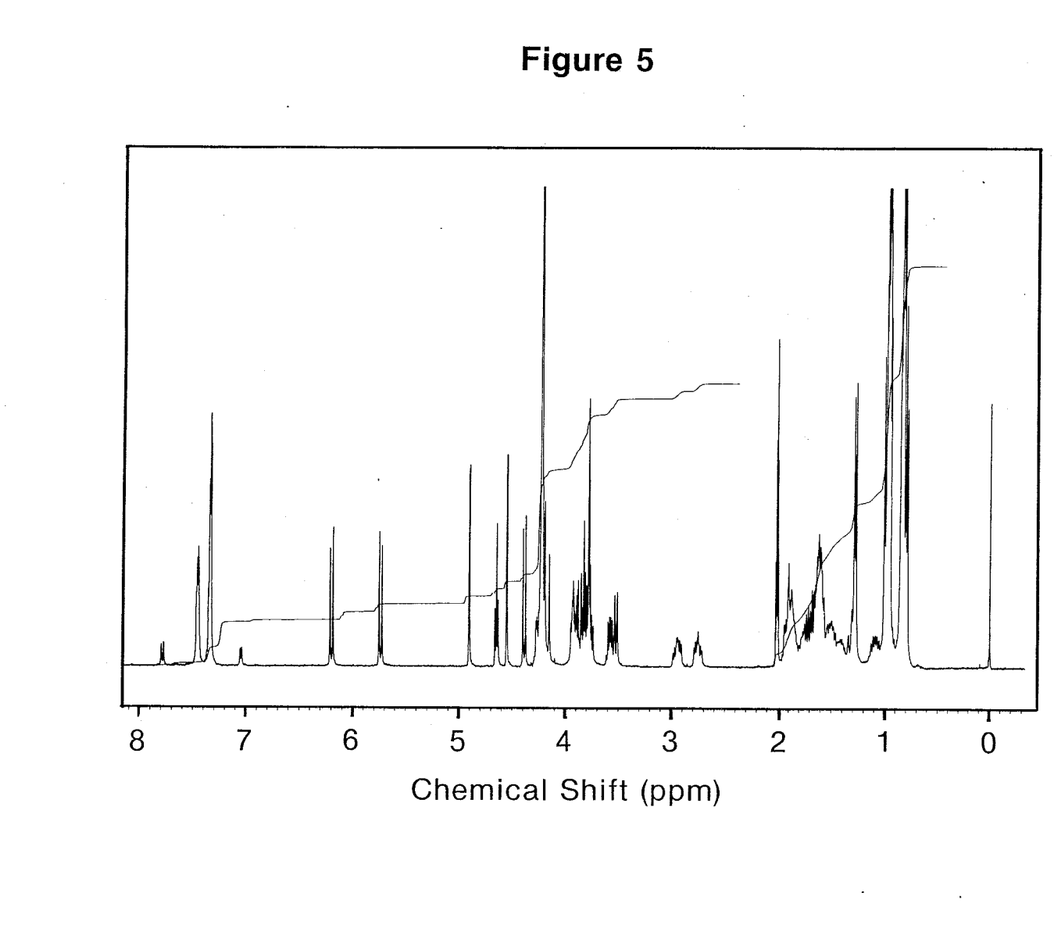
FIG. 5 shows the 400 MHz $^1$H NMR spectrum of the trifluoroacetate salt of EM5587 in deuterated acetonitrile-deuterated water-trifluoroacetic acid (50:50:0.1).

The 400 MHz $^1$H NMR spectrum of the trifluoroacetate salt of EM5587 in deuterated acetonitrile-deuterated water-trifluoroacetic acid (50:50:0.1) is shown in FIG. 5.

Thin layer partition chromatography of the trifluoroacetate salt of EM5587 on Merck silica gel-60, using n-butanol-acetic acid-water (4:1:1) gives an Rf value of 0.42.

The trifluoroacetate salt of EM5587 is soluble in methanol, acetonitrile-water (1:1) and dimethylsulfoxide, but is not substantially soluble in acetonitrile, chloroform, benzene, ethyl acetate or water.

EXAMPLE 2

Desleucyl EM5587 (compound of formula II, R is hydrogen)

Method I

Phenylisothiocyanate (10 ml) was added to a solution of 247.1 mg (0.16 mmol) of EM5587, trifluoroacetate salt in 24.7 ml of 50% aqueous pyridine. The mixture was allowed to stand at 37° C. under an atmosphere of nitrogen for one hour with occasional swirling. Toluene extraction (3×30 ml) removed the excess reagent and other apolar products (50% aqueous pyridine was added as necessary to maintain a biphasic extraction). The aqueous layer was concentrated and lyophilized to yield the phenylthiocarbamyl lysobactin derivative as a white solid (ca. 250 mg). Trifluoroacetic acid (10 ml) was added to the solid derivative and the solution was heated at 80° C. for 10 minutes under a nitrogen atmosphere. After chilling to 0° C., the reaction mixture was diluted with toluene (100 ml) and evaporated to dryness. Diethyl ether trituration (4×10 ml) removed the cleaved amino terminal leucine residue as its thiazolinone, leaving a mixture of degraded peptides. The desleucyl EM5587 trifluoroacetate salt was purified from the degraded peptide mixture by chromatography on a column (2.5 cm×58) of Fractogel TSK-HW40 F in methanol. Fractions were combined on the basis of TLC homogeneity (silica gel, n-butanol-acetic acid-water, 4:1:1, $R_f=0.38$) and evaporated, affording 44.7 mg (0.03 mmol) of the desired product.

Analyses were performed on the product after drying in vacuo for 3 hours at room temperature.

Analysis Calc'd. for $C_{52}H_{86}N_{14}O_{16}.2TFA.H_2O$: C, 45.38; H, 6.67; N, 13.24; F, 7.70. Found: C, 45.73; H, 6.34; N, 13.43; F, 6.4.

The fast atom bombardment (FAB) mass spectrum gave a molecular ion at 1163 m/z $(M+H)^+$ in the positive ion mode and 1161 m/z $(M-H)^-$ in the negative ion mode. The infrared (IR) spectrum in potassium bromide included peaks at 1742 (shoulder) and 1670 $cm^{-1}$.

Method II

One gram of EM5587 trifluoroacetate salt (0.67 mmol) was dissolved in 65 ml of 50% aqueous pyridine and 15 ml of phenylisothiocyanate was added. The solution was purged with a stream of dry nitrogen for 10 minutes, stoppered, and then allowed to stand at 37° C. for one hour with occasional swirling. Toluene extraction (one 50 ml portion followed by two 30 ml portions) removed excess reagent and apolar byproducts. The residual aqueous suspension was concentrated with the aid of n-butanol flotation and then lyophilized to yield the phenylthiocarbamyl derivative of EM5587 as a white solid. The lyophilate was treated with 10 ml of trifluoroacetic acid at 40° C. for 10 minutes under a nitrogen atmosphere. The trifluoroacetic acid was partially removed by evaporation under a stream of nitrogen for 10 minutes and then 60 ml of 0° C. diethyl ether was added to precipitate the peptide. The cleaved leucine thiazolinone derivative was removed by centrifuging and decanting the diethyl ether layer from the precipitated peptide and repeating the process of trituration with two additional portions (60 ml each) of 0° C. diethyl ether. The white precipitate was dried in vacuo overnight at room temperature to yield 959.2 mg (0.69 mmol) of the desired product (homogeneous by TLC, Merck silical gel, n-butanol-acetic acid-water, 4:1:1, $R_f=0.38$). The FAB mass spectrum gave a molecular ion at 1163 m/z $(M+H)^+$ in the positive ion mode and 1161 m/z $(M-H)^-$ in the negative ion mode. The IR spectrum in potassium bromide included peaks at 1744 (shoulder) and 1670 $cm^{-1}$.

EXAMPLE 3

D-Alanyldesleucyl EM5587, trifluoroacetate salt (compound of formula II, R=D-alanyl)

A solution of desleucyl EM5587, trifluoroacetate salt (800 mg, 0.58 mmol), triethylamine (250 μl, 1.8 mmol) and dimethylformamide (50 ml) was prepared, then diluted with 150 ml of solvent mixture A (tetrahydrofuran-ethyl acetate-dimethylformamide 6:2:0.5) and chilled to −65° C. The N-carboxyanhydride of D-alanine (115.7 mg, 1 mmol) was dissolved in 50 ml of solvent mixture A via sonication and was slowly added to the first solution under an atmosphere of nitrogen at −65° C. with rapid stirring. After mixing for 10 minutes, 25 ml of 1M aqueous acetic acid (prechilled to 0° C.) was added with stirring. The reaction mixture was evaporated to an oily residue, from which diethyl ether soluble materials were removed by filtration. The diethyl ether insoluble residue was chromatographed on a 5×42 cm column of CHP20P resin eluting with a linear gradient from 2L of 0.1% aqueous trifluoroacetic acid to 2L of 0.1% trifluoroacetic acid in acetonitrile-water (4:1 v/v) at a flow rate of 4 ml/minute. The antibacterial fractions were pooled on the basis of TLC homogeneity (silica gel, n-butanol-acetic acid-water, 4:1:1, $R_f=0.30$) and lyophilized to provide the desired product (116.3 mg, 0.08 mmol) as a white solid (melting point 206°-212° C.). The FAB mass spectrum gave a molecular ion at 1234 m/z $(M+H)^+$ in the positive ion mode and 1232 m/z $(M-H)^-$ in the negative ion mode. The IR spectrum in potassium bromide showed peaks at 1750 (shoulder) and 1672 $cm^{-1}$.

EXAMPLE 4

L-Alanyldesleucyl EM5587, trifluoroacetate salt (compound of formula II, R=L-alanyl)

A solution of desleucyl EM5587 trifluoroacetate salt (55.3 mg, 40 μmol), triethylamine (25 μl, 180 μmol) and dimethylformamide (5 ml) was prepared, then diluted with 15 ml of solvent mixture A and chilled to −65° C. The N-carboxyanhydride of L-alanine (10.5 mg, 90 μmol) was dissolved in 5 ml of solvent mixture A via sonication and was slowly added to the first solution under an atmosphere of nitrogen at −65° C. with rapid stirring. After mixing for ten minutes, 5 ml of 1M aqueous acetic acid (prechilled to 0° C.) was added with stirring. The reaction mixture was evaporated to an oily residue, from which the diethyl ether soluble materials were removed by trituration. The diethyl ether insoluble residue was chromatographed on a 1.1×57 cm column of CHP20P resin eluting with a linear gradient from 300 ml of 0.1% aqueous trifluoroacetic acid to 300 ml of 0.1% trifluoroacetic acid in acetonitrile-water (3:2 v/v) at a flow rate of 2 ml/minute. The antibacterial fractions were pooled on the basis of TLC homogeneity (silica gel, n-butanol-acetic acid-water, 4:1:1, $R_f=0.30$) and lyophilized to yield the desired product (4.0 mg, 2.8 μmol) as a white solid. The FAB mass spectrum gave a molecular ion at 1234 m/z $(M+H)^+$ in the positive ion mode and 1232 m/z $(M-H)^-$ in the negative ion mode. The IR spectrum in potassium bromide showed peaks at 1750 (shoulder) and 1672 $cm^{-1}$.

EXAMPLE 5 n-Propionyldesleucyl EM5587 (compound of formula II, R=n-propionyl)

Desleucyl EM5587, trifluoroacetate salt (5 mg) was dissolved in dry dimethylformamide (0.5 ml) containing triethylamine (2 μl), and a mixture of n-propionyl chloride (0.25 μl) in dry dimethylformamide (0.75 μl) was then added. The reaction was stirred at room temperature for 2 hours and the product was detected by the appearance of antibiotic activity. The FAB mass spectrum of the crude reaction mixture showed the molecular ion at 1219 m/z $(M+H)^+$ in the positive ion mode.

EXAMPLE 6

Glycyldesleucyl EM5587 (compound of formula II, R=glycyl)

1-Hydroxybenzotriazole (0.6 mg) and N-benzyloxycarbonylglycine (0.9 mg) were dissolved in 100 μl of dry dimethylformamide at 0° C. After stirring for 10 minutes, N,N'-dicyclohexylcarbodiimide (3.2 mg) was added to the solution and stirring was continued for 3 hours at 0° C. A suspension of desleucyl EM5587 trifluoroacetate salt (7.7 mg) and sodium bicarbonate (2.6 mg) was prepared in 100 μl of dimethylformamide and the soluble portion of the suspension was added to the cold reaction mixture. The acylation reaction was allowed to warm to room temperature gradually while stirring overnight. Aqueous 1M acetic acid (1 ml) and catalyst (5% palladium on charcoal) were added to the reaction mixture that was then stirred vigorously under a hydrogen atmosphere for 4.5 hours at room temperature. The catalyst was removed by filtration through diatomaceous earth and the crude product was evaporated to an oily residue. The desired product was detected by the appearance of a new antibacterial substance by TLC. The FAB mass spectrum of the crude product gave a molecular ion at 1220 m/z (M+H)+ in the positive ion mode.

Biological Activity

For aerobic bacteria, the minimum inhibitory concentrations (MIC) of some of the compounds of this invention were determined by an agar dilution technique. The test organisms were prepared from frozen stocks and diluted to give a final level of $10^7$ CFU/ml. The test compounds were dissolved in the appropriate diluent at a concentration of 1,000 μg/ml. Two fold dilutions were made in Yeast Beef Broth (Difco), resulting in a range from 1,000 μg/ml to 0.5 μg/ml. A 1.5 ml sample of each dilution was placed into individual petri dishes to which 13.5 ml of K-10 agar* was added. The final drug concentration in the agar ranged from 100 μg/ml to 0.05 μg/ml. Organism growth control plates containing agar only were prepared and inoculated before and after the test plates. The organisms were applied to the surface of each plate with the Denley Multipoint Inoculator (which delivers approximately 0.001 ml of each organism) resulting in a final inoculum level of $10^4$ CFU on the agar surface.

The plates were incubated at 37° C. for 18 hours and the MIC's then determined. The MIC is the lowest concentration of compound inhibiting growth of the organism.

The results of the agar dilution assays are as follows.

| *K-10 agar is | |
|---|---|
| Beef extract | 1.5 g |
| Yeast extract | 3.0 g |
| Peptone | 6.0 g |
| Dextrose | 1.0 g |
| Agar | 15.0 g |
| Distilled water to | 1000 ml |

| Organism | SC No.* | EM5587, TFA salt MIC (μg/ml) |
|---|---|---|
| *Staphylococcus aureus* | 1276 | 0.2 |
| *Staphylococcus aureus* | 2399 | 0.2 |
| *Staphylococcus aureus* (Penicillin$^R$)** | 2400 | 0.2 |
| *Staphylococcus aureus* | 10165 | 0.2 |
| *Staphylococcus aureus* (Methicillin$^R$) | 3184 | 1.6 |
| *Staphylococcus aureus* (Methicillin$^R$) | 10014 | 0.2 |
| *Staphylococcus aureus* (Methicillin$^R$) | 10020 | 0.4 |
| *Staphyloccus aureus* (Gentamicin$^R$) | 11239 | 0.4 |
| *Staphyloccus aureus* (Erythromycin$^R$) | 10820 | 0.8 |
| *Streptococcus faecalis* | 9011 | 0.8 |
| *Streptococcus agalactiae* | 9287 | 0.4 |
| *Micrococcus luteus* | 2495 | 0.2 |
| *Escherichia coli* | 8294 | 12.5 |
| *Escherichia coli* | 10857 | 3.1 |
| *Escherichia coli* | 10896 | 6.3 |
| *Escherichia coli* | 10909 | 3.1 |
| *Klebsiella aerogenes* | 10440 | 25 |
| *Klebsiella pneumoniae* | 9527 | 50 |
| *Proteus mirabilis* | 3855 | >50 |
| *Proteus rettgeri* | 8479 | 50 |
| *Proteus vulgaris* | 9416 | 12.5 |
| *Salmonella typhosa* | 1195 | 25 |
| *Shigella sonnei* | 8449 | 12.5 |
| *Enterobacter cloacae* | 8236 | 25 |
| *Enterobacter aerogenes* | 10078 | 25 |
| *Citrobacter freundii* | 9518 | 50 |
| *Serratia marcescens* | 9783 | 25 |
| *Pseudomonas aeruginosa* | 9545 | 25 |
| *Pseudomonas aeruginosa* | 8329 | 25 |
| *Acinetobacter calcoaceticus* | 8333 | 12.5 |

*SC No is the number of the microorganism in the collection of E. R. Squibb & Sons, Inc. Princeton, New Jersey
**($^R$) indicates that the organism is resistant to the antibiotic named.

| Organism | SC No.* | EM5587 TFA salt MIC (μg/ml) | desleucyl EM5587 TFA salt MIC (μg/ml) | D-alanyl desleucyl EM5587 TFA salt MIC (μg/ml) | L-alanyl desleucyl EM5587 TFA salt MIC (μg/ml) |
|---|---|---|---|---|---|
| *Staphylococcus aureus* | 1276 | 0.2 | 50 | 0.4 | 3.1 |
| *Staphylococcus aureus* | 2399 | 0.2 | 100 | 0.4 | 6.3 |
| *Staphylococcus aureus* (Penicillin ®)** | 2400 | 0.2 | 50 | 0.4 | 6.3 |
| *Staphylococcus aureus* | 10165 | 0.2 | 100 | 0.8 | 12.5 |
| *Streptococcus faecalis* | 9011 | 0.8 | 50 | 1.6 | 6.3 |
| *Streptococcus agalactiae* | 9287 | 0.4 | 50 | 0.2 | 3.1 |
| *Micrococcus luteus* | 2495 | 0.2 | 50 | 0.1 | 1.6 |
| *Escherichia coli* | 8294 | 12.5 | >100 | 50 | >100 |
| *Escherichia coli* | 10857 | 3.1 | >100 | 12.5 | 100 |
| *Escherichia coli* | 10896 | 6.3 | >100 | 6.3 | 25 |
| *Escherichia coli* | 10909 | 3.1 | >100 | 3.1 | 12.5 |
| *Klebsiella aerogenes* | 10440 | 25 | >100 | 100 | >100 |
| *Klebsiella pneumoniae* | 9527 | 50 | >100 | 100 | >100 |
| *Proteus mirabilis* | 3855 | >50 | >100 | >100 | >100 |
| *Proteus rettgeri* | 8479 | 50 | >100 | 100 | >100 |
| *Proteus vulgaris* | 9416 | 12.5 | >100 | 50 | 100 |
| *Salmonella typhosa* | 1195 | 25 | >100 | 50 | >100 |
| *Shigella sonnei* | 8449 | 12.5 | >100 | 25 | 100 |
| *Enterobacter cloacae* | 8236 | 25 | >100 | 100 | >100 |

| Organism | SC No.* | EM5587 TFA salt MIC (μg/ml) | desleucyl EM5587 TFA salt MIC (μg/ml) | D-alanyl desleucyl EM5587 TFA salt MIC (μg/ml) | L-alanyl desleucyl EM5587 TFA salt MIC (μg/ml) |
|---|---|---|---|---|---|
| Enterobacter aerogenes | 11078 | 25 | >100 | 100 | >100 |
| Citrobacter freundii | 9518 | 50 | >100 | 100 | >100 |
| Serratia marcescens | 9783 | 25 | >100 | >100 | >100 |
| Pseudomonas aeruginosa | 9545 | 25 | >100 | >100 | >100 |
| Pseudomonas aeruginosa | 8329 | 25 | >100 | >100 | >100 |
| Acinetobacter calcoaceticus | 8333 | 12.5 | >100 | 50 | >100 |

The susceptibility of a number of anaerobic bacteria to EM5587, trifluoroacetate salt was also determined by an agar dilution technique. Test organisms were prepared from 24–48 hour cultures grown in Chopped Meat Broth (Scott Laboratories, Fiskeville, R.I.), or from washings from chocolate agar slants. These slants were prepared by adding hemoglobin to Protease #3 agar (Difco) to a concentration of 1 percent. The growth was washed off the slants with Brain Heart Infusion Broth (BBL Microbiology Systems) and diluted to a density of $1 \times 10^8$ CFU/ml. The trifluoroacetate salt of EM5587 was dissolved in the appropriate diluent at a concentration of 1,000 μg/ml. Two fold dilutions were made in Yeast Beef Broth (Difco) resulting in a range from 1,000 μg/ml. A 1.5 ml sample of each dilution was placed into individual petri dishes to which 13.5 ml of DST agar (Oxoid USA, Inc. Red Branch Road, Columbia, Md.) containing 5% lysed sheep blood and 0.5 μg/ml vitamin K was added. The final drug concentration in the agar ranged from 100 μg/ml to 0.05 μg/ml. Organism growth control plates containing agar only were prepared and inoculated before and after the test plates. The organisms were applied to the surface of each plate with the Denly Multipoint Inoculator (which delivers approximately 0.001 ml of each organism) resulting in a final inoculum level of $10^5$ CFU on the agar surface. Plates were incubated at 37° C. for 18 hours in an anaerobic chamber (Forma Scientific, Marietta, Ohio) and the MIC values then determined. The MIC is the lowest concentration of antibiotic inhibiting growth of the organism.

The results of the agar dilution assays are:

| Organism | SC No. | EM5587 TFA salt MIC (μg/ml) |
|---|---|---|
| Clostridium difficile | 11251 | 0.2 |
| Clostridium perfringens | 11256 | 0.4 |
| Clostridium histolyticum | 8572 | 0.8 |
| Clostridium septicum | 1780 | 0.1 |
| Peptococcus variabilis | 11264 | 0.2 |
| Peptostreptococcus anaerobius | 11263 | 0.8 |
| Propionibacterium acnes | 4020 | 0.1 |
| Eubacterium lentum | 11261 | 0.4 |
| Bifidobacterium dentium | 11260 | 0.4 |
| Hemophilus vaginalis | 8568 | 0.8 |
| Hemophilus vaginalis | 9640 | 0.8 |
| Fusobacterium necrophorum | 10338 | 25.0 |
| Bacteroides fragilis | 9844 | 50.0 |
| Bacteroides fragilis | 10277 | 25.0 |
| Bacteroides thetaiotaomicron | 9005 | 12.5 |
| Bacteroides thetaiotaomicron | 10278 | 25.0 |

What is claimed is:

1. A compound having the formula or a pharmaceutically acceptable salt thereof, wherein R is hydrogen or acyl.

2. A compound in accordance with claim 1 wherein R is hydrogen.

3. A compound in accordance with claim 1 wherein R is acyl.

4. A compound in accordance with claim 1 wherein R is D-leucyl.

5. A compound in accordance with claim 1 wherein R is D-alanyl.

6. A compound in accordance with claim 1 wherein R is L-alanyl.

7. A compound in accordance with claim 1 wherein R is glycyl.

8. A compound in accordance with claim 1 wherein R is n-propionyl.

* * * * *